United States Patent [19]

Jozic

[11] Patent Number: 4,485,108

[45] Date of Patent: Nov. 27, 1984

[54] 1-NAPHTHALENESULFONAMIDES, THEIR PHARMACEUTICAL COMPOSITIONS AND METHOD OF USE

[75] Inventor: Ljerka Jozic, Hanover, Fed. Rep. of Germany

[73] Assignee: Beecham Wuelfing GmbH & Co., KG, Fed. Rep. of Germany

[21] Appl. No.: 423,441

[22] Filed: Sep. 24, 1982

[30] Foreign Application Priority Data

Sep. 24, 1981 [GB] United Kingdom ............... 8128857

[51] Int. Cl.$^3$ ............... A61K 31/495; A61K 31/445; A61K 31/40; C07D 295/12
[52] U.S. Cl. .................... 424/267; 424/274; 424/248.5; 424/250; 546/205; 546/206; 544/159; 544/398; 548/569
[58] Field of Search ............... 544/159, 398; 546/205, 546/206; 548/569; 424/248.5, 250, 267, 274

[56] References Cited

U.S. PATENT DOCUMENTS 4,372,955 2/1983 Jozic .................................. 546/205
4,436,908 3/1984 Jozic .................................. 546/206

FOREIGN PATENT DOCUMENTS 26072 4/1983 European Pat. Off. ........... 546/205

*Primary Examiner*—Robert T. Bond
*Attorney, Agent, or Firm*—Jacobs & Jacobs

[57] ABSTRACT

Compounds of the formula (I) and salts thereof:

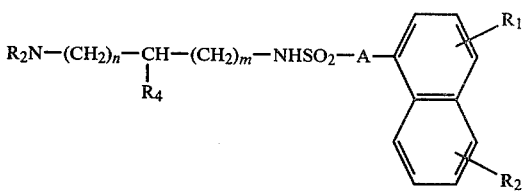

wherein:

A is a bond, —$CH_2$— or —CH=CH—;

$R^2$ is hydrogen and $R^1$ is selected from $C_{1-4}$ alkyl, hydroxyl, $C_{1-4}$ alkoxy, $C_{1-4}$ alkanoyloxy, hydrogen, halogen, nitro, cyano, and amino optionally substituted by one or two $C_{1-4}$ alkyl groups or by $C_{1-4}$ alkanoyl;

$R^4$ is $C_{1-4}$ alkyl, hydroxy, $C_{1-4}$ alkoxy, $C_{1-4}$ alkanoyloxy or nitrato;

$R_2$N is 1-piperidyl, morpholino or 4-methyl-1-piperazyl, optionally substituted by one or two methyl groups in the 2-, 4- or 6- positions as apt, or 1-pyrrolidyl substituted by one or two methyl groups.

m is 0 or 1; and n is 0 to 3 a process for their preparation and compositions containing them.

14 Claims, No Drawings

1-NAPHTHALENESULFONAMIDES, THEIR PHARMACEUTICAL COMPOSITIONS AND METHOD OF USE

This invention relates to anti-arrhythmic agents, to pharmaceutical compositions containing them, and to a process for their preparation.

The present invention provides the compounds of the formula (I) and salts thereof:

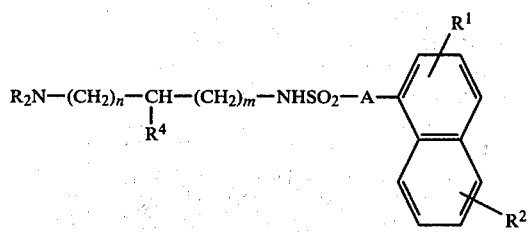

wherein:

A is a bond, —$CH_2$— or —CH=CH—; one of $R^1$ and $R^2$ is hydrogen and the other is selected from $C_{1-4}$ alkyl, hydroxyl, $C_{1-4}$ alkoxy, $C_{1-4}$ alkanoyloxy, hydrogen, halogen, nitro, cyano, and amino optionally substituted by one or two $C_{1-4}$ alkyl groups or by $C_{1-4}$ alkanoyl;

$R^4$ is $C_{1-4}$ alkyl, hydroxy, $C_{1-4}$ alkoxy, $C_{1-4}$ alkanoyloxy or nitrato;

$R_2N$ is 1-pyrrolidyl, 1-piperidyl, morpholino or 4-methyl-1-piperazyl, optionally substituted by one or two methyl groups;

m is 0 or 1; and
n is 0 to 3.

In a group of compounds of formula (I) $R^2$ is hydrogen and $R^1$ is as hereinbefore defined, and $R_2N$ is 1-piperidyl, morpholino or 4-methyl-1-piperazyl, optionally substituted by one or two methyl groups in the 2-, 4- or 6-positions as apt, or 1-pyrrolidyl substituted by one or two methyl groups.

In a second group of compounds $R^1$ is selected from $C_{1-4}$ alkoxy, $C_{1-4}$ alkanoyloxy, hydrogen, halogen, nitro, cyano and amino optionally substituted by one or two $C_{1-4}$ alkyl groups or by $C_{1-4}$ alkanoyl.

In a sub-group of these compounds $R_2N$ is 1-pyrrolidyl substituted by one or two methyl groups.

In a second sub-group $R_2N$ is 1-piperidyl.

In a third sub-group $R_2N$ is 1-piperidyl substituted by one or two methyl groups, in the 2-, 4- or 6-positions, and $R^4$ is $C_{1-4}$ alkyl.

In a fourth sub-group $R_2N$ is morpholino or 4-methyl-1-piperazyl optionally substituted by one or two methyl groups, in the 2- or 6-positions.

In this group of compounds and its sub-groups $R^1$ is favourably selected from $C_{1-4}$ alkoxy, hydrogen, nitro, cyano and optionally substituted amino as defined.

In a third group of compounds $R^1$ is $C_{1-4}$ alkyl.

In a sub-group of these compounds $R_2N$ is 1-pyrrolidyl substituted by one or two methyl groups.

In a second sub-group $R_2N$ is 1-piperidyl.

In a third sub-group $R_2N$ is 1-piperidyl substituted by one or two methyl groups in the 2-, 4- or 6-positions.

In a fourth sub-group $R_2N$ is morpholino or 4-methyl-1-piperazyl optionally substituted by one or two methyl groups in the 2- or 6-positions.

Apt values for $NR_2$ include 1-piperidyl, 2-methyl-1-pyrrolidyl, 3-methyl-1-pyrrolidyl, 2,3-dimethyl-1-pyrrolidyl, 2,4-dimethyl-1-pyrrolidyl, 2,5-dimethyl-1-pyrrolidyl. Other apt values for $NR_2$ include 2-methyl-1-piperidyl, morpholino and 4-methylpiperazyl.

Favoured values for $NR_2$ include 2-methylpiperidyl, favoured values for $NR_2$ also include 2,4-dimethylpyrrolidyl.

A is preferably a bond.

Apt values for $R^4$, $R^1$, $R^2$ $C_{1-4}$ alkyl groups include methyl, ethyl and n- and iso-propyl preferably methyl.

Apt values for $R^4$, $R^1$ and $R^2$ $C_{1-4}$ alkoxy groups include methoxy, ethoxy and n- and iso-propoxy preferably methoxy.

Apt values for $C_{1-4}$ alkanoyl for $R^1$ or within $R^4$ include acetyl and propionyl, preferably acetyl.

Suitable $R^4$ include methyl, ethyl, hydroxy; methoxy, ethoxy, isopropoxy; acetoxy, propionoxy; and nitrato; preferably methyl and hydroxy.

Suitable $R^1$ include methyl, ethyl, isopropyl, fluorine, chlorine, bromine and iodine. Suitable $R^1$ also include methoxy.

Preferred $R^1$ values include methoxy. Preferred $R^1$ values also include methyl.

Suitable $R^2$ include hydrogen.

n may be 0 to 3, more suitably 1 or 3, preferably 1 when $R^4$ is (derivatised) hydroxy and preferably 3 when $R^4$ is $C_{1-4}$ alkyl.

From the foregoing it will be appreciated that a group of compounds of formula (I) are of formula (II):

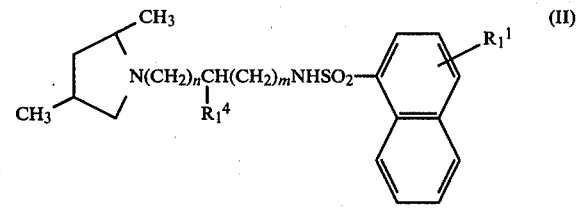

wherein: $R^1_1$ is $C_{1-4}$ alkoxy, $C_{1-4}$ alkyl or hydrogen; $R^4_1$ is methyl or hydroxy; and the remaining variables are as defined in formula (I).

Suitable and preferred m and n are as so described hereinbefore. Suitable and preferred $R^1_1$, and $R^4_1$ are as so described for relevant $R^1$ and $R^4$ hereinbefore.

A sub-group of formula (II) is of formula (III):

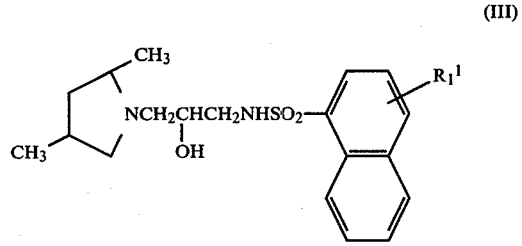

wherein: $R^1_1$ is as hereinbefore defined.

Preferably the $R^1_1$ group is in the 4-position, in particular 4-methoxy, or in the 2-position, in particular 2-methyl, or is hydrogen.

A second sub-group of formula (II) is of formula (IV):

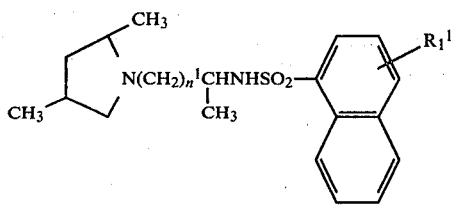

wherein: $R^1_1$ is hereinbefore defined, and $n^1$ is 1 or 3.

Preferably the $R^1_1$ group is in the 4-position, in particular 4-methoxy, or in the 2-position, in particular methyl, or is hydrogen.

$n^1$ is preferably 3.

A second group of compounds of formula (I) is of formula (V):

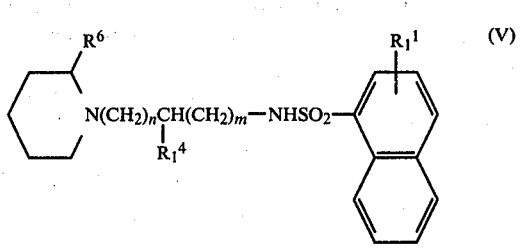

wherein: $R^6$ is hydrogen or methyl, and the remaining variables are as hereinbefore defined.

Suitable and preferred variables are as so described under formula (II).

A sub-group of formula (V) is of formula (VI):

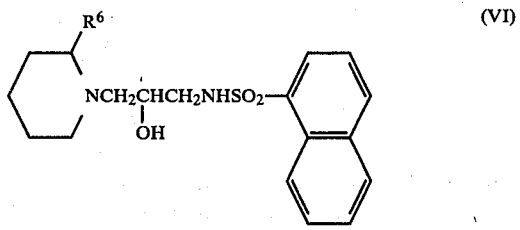

wherein: $R^6$ is hydrogen or methyl.

Preferably the $R^1_1$ group is in the 4-position, in particular 4-methoxy, or is hydrogen.

A second sub-group of formula (V) is of formula (VII):

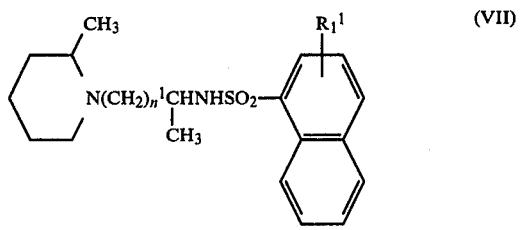

wherein:
$R^1_1$ is as defined in formula (III); and
$n^1$ is 1 or 3, in particular 3.
$n^1$ is preferably 3.

Preferably the $R^1_1$ group is in the 4-position, in particular 4-methoxy, or is hydrogen.

It will of course be realised that when $NR_2$ in the compounds of the formula (I) is asymmetrically substituted by one methyl group, the $NR_2$ group has a chiral centre.

Compounds of the formula (I) containing such $NR_2$ groups are the thus capable of existing in a number of stereoisomeric forms.

When $NR_2$ is substituted by two methyl groups, these may give rise to different isomers wherein the two groups are mutually cis or trans across the ring.

The invention extends any of the stereoisomeric forms including enantiomers of the compounds of the formula (I) and to mixtures thereof, including racemates. The different stereoisomeric forms may be separated one from the other by the usual methods, or any given isomer may be obtained by stereospecific or asymmetric synthesis.

The salts of the compounds of the formulae (I) to (VII) include acid addition salts and are preferably acid addition salts with pharmaceutically acceptable acids. Such acids may be inorganic or organic acids such as hydrochloric, hydrobromic, sulphuric, methanesulphonic, acetic, citric, lactic, tartaric, propionic, benzoic, fumaric and the like.

The salts of the compounds of the formula (I), to (VII) also include pharmaceutically acceptable quaternary ammonium salts. Examples of such salts include such compounds quaternised by compounds such as $R^5$-Y wherein $R^5$ is $C_{1-6}$ alkyl, phenyl-$C_{1-6}$ alkyl or $C_{5-7}$ cycloalkyl, and Y is an anion of an acid. Suitable examples of $R^5$ include methyl, ethyl and n- and iso-propyl; and benzyl and phenylethyl. Suitable examples of Y include the halides such as chloride, bromide and iodide.

Examples of salts also include pharmaceutically acceptable internal salts such as N-oxides.

The present invention provides a pharmaceutical composition comprising a compound of the formula (I) or a pharmaceutically acceptable salt thereof, together with a pharmaceutically acceptable carrier.

The composition of this invention may be adapted for administration by mouth or by injection. Most suitably the composition will be in unit-dose form and such unit-doses will normally contain from 1 mg to 100 mg and more usually from 2 mg to 50 mg of the active agent.

These compositions may be administered 1 to 6 times daily or more usual 2 to 4 times daily in such a manner that the daily dose for a 70 kg adult is about 1 mg to 250 mgs and more usually 5 mg to 200 mg, for example 10 mg to 75 mg. The compositions of this invention may be fabricated in conventional manner, for example they may be presented as tablets or capsules for oral administration or as dry powders sealed into ampoules for reconstitution with water or saline for injection. Tablets and capsules may contain carriers such as disintegrants, binders, lubricants, colorants and the like in conventional manner. They may therefore contain such agents as microcrystalline cellulose, lactose, starch, polyvinylpyrrolidone, sodium starch glycollate, magnesium stearate and the like. Tablets may be prepared by conventional mixing and compressing operations and capsules may be presented by conventional mixing and filling operations.

The invention also provides a method of treatment or prophylaxis of cardiac arrhythmia in mammals including humans, comprising the administration to a sufferer of a therapeutically effective amount of a compound of the formula (I) or a pharmaceutically acceptable salt thereof.

The present invention also provides a process for the preparation of a compound of the formula (I), comprising the reaction of a compound of the formula (VIII):

$$R_2N(CH_2)_nCHR_4(CH_2)_mNH_2 \quad (VIII)$$

wherein the variables are as defined in relation to formula (I) and a compound of the formula (IX):

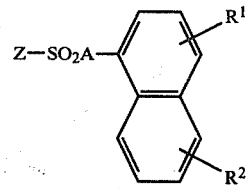

(IX)

wherein Z is a group readily displaceable by a nucleophile, such as chlorine or bromine and $A, R^1_1$ and $R^2_1$ are as hereinbefore defined; and optionally forming a salt of the resultant compound of the formula (I).

The preceding condensation reaction is generally effected at ambient temperature and normal pressure in a convenient solvent such as benzene or toluene optionally in the presence of a base. Removal of the solvent, for example by evaporation, yields the initial crude product, which will generally be the desired compound as free or its salt depending on whether the reaction is carried out in the presence or absence of a base. The free basic product may be purified by crystallisation or chromatography; or a salt may be purified by crystallisation. If desired a salt may be converted into the free base by neutralisation and if desired the free base may be conventionally salified or the reaction effected in the presence of base to give the free base.

When both of $R^1$ and $R^2$ are not hydrogen in a compound of the formula (I), interconversion of suitable substituents may be carried out by conventional methods after formation of a compound of the formula (I). By way of example an acetamido group may be converted to an amino group, an alkoxyl or acetoxyl group may be converted to a hydroxyl group or a nitro group may be group may be reduced to an amino group, all by conventional methods. Accordingly it will be realised that compounds of the formula (I) containing a substituent on the 1-naphthyl group which is convertible to another substituent group are useful intermediates and as such form an important aspect of the invention.

It will also be realised that salts of the compounds of the formula (I) which are not pharmaceutically acceptable may be useful as intermediates in the preparation of pharmaceutically acceptable salts of compounds of the formula (I) or the compounds of the formula (I) themselves, and as such form an aspect of the present invention.

When $NR_2$ in the compounds of the formula (I) is substituted by two methyl groups, these may be mutually cis or trans about the $NR_2$ ring. A mixture of cis and trans isomers of the compound of the formula (I) may be synthesised non stereospecifically and the desired isomer separated conventionally therefrom, e.g. by chromatography; or alternatively the cis or trans isomer may if desired be synthesised from the corresponding cis or trans form of the compound of the formula (VIII).

Cis- and trans-forms of the compound of the formula (VIII) are either known as separate forms or may be separated conventionally e.g. by chromatography.

Racemates of compounds of the formula (I) wherein $NR_2$ is substituted by one or two methyl groups may be resolved conventionally, e.g. by salification with a chiral acid and separation of the resultant salts.

The following Examples illustrate the invention.

EXAMPLE 1

1-[2-(4-methoxy-1-naphthalenesulphonamido)propyl]-2-methylpiperidinium chloride (1)

A solution of 1-(2-aminopropyl)-2-methylpiperidine (4.5 g, 0.029 mol) and triethylamine (2.9 g; 0.029 mol) in toluene (20 ml) was added dropwise to a solution of 4-methoxy-1-naphthalenesulphonylchloride (7.9 g; 0.032 mol) in toluene (180 ml) at room temperature. Thereafter, the mixture was stirred for a further 4 hours until the reaction was complete and the reaction mixture was extracted twice with water (100 ml). The toluene solution was dried over $Na_2SO_4$ and neutralized with a solution of HCl in ethanol. The reaction product separated as an oil. The reaction mixture was evaporated and residue dissolved in isopropanol (150 ml) and boiled with charcoal. The charcoal was filtered off, and reaction product crystallized from the solution (8.9 g).

Mp: 172° C.

Yield: 74% of theoretical.

Compounds (2) and (4), (5), (6) and (8) were prepared in the same manner, with immaterial work-up variations.

Compounds (3) and (7) were prepared analogously, but the chloride was neutralized and the resultant free base was isolated. The compounds of Tables 3 and 4 are prepared similarly.

EXAMPLE 2

1-[2-hydroxy-3-(1-naphthalenesulphonamido)propyl]-1-methylpyrrolidinium iodide (9)

To a solution of 1-[2-hydroxy-3-(1-naphthalenesulphonamido)propyl]pyrrolidine (2 g; 0.0005 mol) in methanol (50 ml) was added methyl iodide (6.9 g; 0.05 mol). The mixture was left at room temperature 12 hours. The reaction mixture was evaporated to dryness and the residue was recrystallized from ethanol (20 ml) to obtain the product (1.3 g).

Mp: 145° C.

Yield: 4% of theoretical.

PHARMACOLOGY OF COMPOUNDS

Test Procedure to Demonstrate Antiarrythmic Effects

Electrostimulation Test

According to the method described by SZEKERES, L. and PAPP, G. J., (Naunyn-Schmiedebergs Arch. exp. Path. Pharmak. 245, 70 (1963), arrhythmias are induced in Guinea pigs by electrostimulation of the right ventricle of the heart. The animals are anesthetized with Urethane (1.2 g/kg i.p.) and artificially respired before a needle electrode is inserted in the right ventricle of the heart. Substances are given intraduodenally 30 min before the stimulation. The voltage needed for induction of extrasystoles in control animals (n=6) is compared with that required for induction of arrhythmias in treated animals (n=6). The difference is statistically evaluated by the unpaired t-test (STUDENT).

This method was used to evaluate the compounds of the present invention. The results are shown in following Tables 1 and 2.

A blank in the last column indicates data not available. * means statistically significant $p<0.05$.

The following abbreviations are used in Tables 1 and 2.

A: acetone
EA: ethyl acetate
IPA: isopropanol

TABLE 1

$$A-(CH_2)_n-\underset{\underset{CH_3}{|}}{CH}-NHSO_2-\text{[naphthyl with } R_1, R_3\text{]}$$

| Compound No. | A | n | $R_1$ | $R_3$ | Salt | Mp °C. | Yield | % Increase of Voltage/ Electrostimulation Test Dose mg/kg i.d. (GP; n = 6) |
|---|---|---|---|---|---|---|---|---|
| (1) | 2-methylpiperidinyl (CH3) | 1 | H | OCH3 | HCl | 172 IPA | 74 | 124,2 * (32) |
| (2) | 4-methylpiperidinyl (CH3) | 1 | H | OCH3 | HCl | 223-4 EtOH | 73 | 15,2 * (32) |
| (3) | 2-methylpiperidinyl (CH3) | 3 | H | H | — | 100 EtOH | 15,3 | 66.7 * (17) |
| (14) | 3,4-dimethylpyrrolidinyl (CH3, CH3) | 3 | H | H | HCl | oil | | |

$$A-(CH_2)_n-\underset{\underset{CH_3}{|}}{CH}(CH_2)_m NHSO_2-\text{[naphthyl with } R_1, R_3\text{]}$$

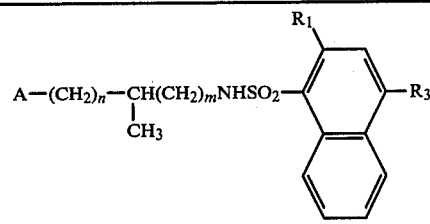

| Compound No. | A | n | $R_1$ | $R_3$ | $R_4$ | Salt | Mp °C. | Yield | % Increase of Voltage/ Electrostimulation Test Dose mg/kg i.d. (GP; n = 6) |
|---|---|---|---|---|---|---|---|---|---|
| (7) | 3,4-dimethylpyrrolidinyl (CH3, CH3) | 3 | H | H | Cl | HCl ½ H2O | 137 A/EA | 52 | |
| (11) | 2-methylpyrrolidinyl (CH3) | 1 | H | H | H | fumarate | 107-110 A/EA | 56 | 43 * (32) |

TABLE 1-continued

| | | | | | | | | | |
|---|---|---|---|---|---|---|---|---|---|
| (15) | ![pyrrolidine with 2,5-diCH3] | 2 | H | OCH3 | H | HCl | 168-9 EA/IPA | 63 | 132 * (8.7) |
| (26) | ![pyrrolidine with 2,5-diCH3] | 3 | CH3 | H | H | HCl | 180-2 A/El20 | 46 | |

TABLE 2

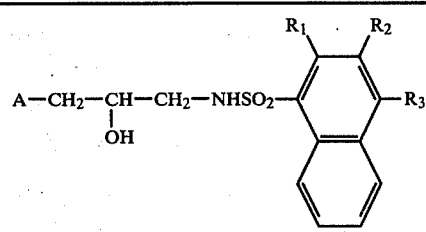

A—CH2—CH(OH)—CH2—NHSO2—[naphthyl with R1, R2, R3]

| Compound No. | A | R1 | R2 | R3 | Salt | Mp °C. | Yield | % Increase of Voltage/ Electrostimulation Test Dose mg/kg i.d. (GP; n = 6) |
|---|---|---|---|---|---|---|---|---|
| (4) | 3-methyl-2-methylpyrrolidine | H | H | H | — | 119 EtOH/Et2O | 10,4 | 23 * (32) |
| (5) | 2-methylpiperidine | H | H | H | HCl | 104 EtOH/Et2O | 13,9 | 50 * (32) |
| (6) | piperidine | H | H | H | HCl | 194 EtOH | 49.3 | 43 * (32) |
| (8) | pyrrolidine | H | H | H | HCl | 180 EtOH | 51,7 | 12 * |
| (9) | pyrrolidine | H | H | H | CH3I | 145 EtOH | 7,8 | 53 * |

TABLE 3

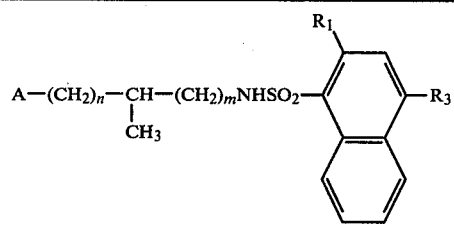

A—(CH₂)ₙ—CH—(CH₂)ₘNHSO₂—[naphthalene with R₁, R₃]
         |
         CH₃

| Compound No. | A | m | n | R₁ | R₃ |
|---|---|---|---|---|---|
| (10) | 2-methylpiperidin-1-yl | 0 | 0 | H | H |
| (12) | 2-methylpiperidin-1-yl | 0 | 2 | H | H |
| (13) | 2-methylpiperidin-1-yl | 1 | 0 | H | H |
| (16) | 2-methylpiperidin-1-yl | 0 | 0 | H | OCH₃ |
| (17) | 2-methylpiperidin-1-yl | 1 | 0 | H | OCH₃ |
| (18) | 2-methylpiperidin-1-yl | 0 | 3 | CH₃ | H |
| (19) | 2-methylpiperidin-1-yl | 0 | 3 | CH₃O | H |
| (20) | 2-methylpiperidin-1-yl | 0 | 3 | OH | H |
| (21) | 2-methylpiperidin-1-yl | 0 | 3 | O.COCH₃ | H |

TABLE 4

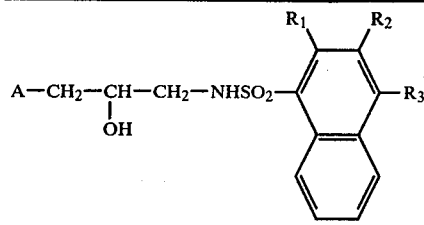

A—CH₂—CH—CH₂—NHSO₂—[naphthalene with R₁, R₂, R₃]
         |
         OH

| Compound No. | A | R₁ | R₂ | R₃ |
|---|---|---|---|---|
| (22) | 2-methylpiperidin-1-yl | H | H | OAc |
| (23) | 2-methylpiperidin-1-yl | H | H | Cl |
| (24) | 2-methylpiperidin-1-yl | H | H | NO₂ |
| (25) | 2-methylpiperidin-1-yl | H | H | CN |

I claim:

1. A compound of the formula (I) or a pharmaceutically acceptable salt thereof:

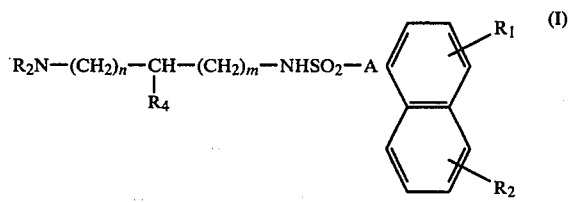

R₂N—(CH₂)ₙ—CH—(CH₂)ₘ—NHSO₂—A—[naphthalene with R₁, R₂]     (I)
             |
             R₄ wherein:
A is a bond;
R² is hydrogen and R¹ is selected from C₁₋₄ alkyl, hydroxyl, C₁₋₄ alkoxy, C₁₋₄ alkanoyloxy, hydrogen, halogen, nitro, cyano, and amino optionally substituted by one or two C₁₋₄ alkyl groups or by C₁₋₄ alkanoyl;
R⁴ is C₁₋₄ alkyl or hydroxy;
R₂N is 1-piperidyl substituted by one or two methyl groups in the 2-, 4- or 6-positions or 1-pyrrolidyl substituted by one or two methyl groups.
m is 0 or 1; and
n is 0 to 3.

2. A compound according to claim 1 wherein:
R² is hydrogen and R¹ is selected from C₁₋₄ alkoxy, C₁₋₄ alkanoyloxy, hydrogen, halogen, nitro, cyano and amino optionally substituted by one or two C₁₋₄ alkyl groups or by C₁₋₄ alkanoyl.

3. A compound according to claim 2 wherein $R_2N$ is 1-pyrrolidyl substituted by one or two methyl groups.

4. A compound according to claim 2 wherein $R_2N$ is 1-piperidyl substituted by one or two methyl groups.

5. A compound according to claim 2 wherein $R^2$ is selected from $C_{1-4}$ alkoxy, hydrogen, nitro, cyano and optionally substituted amino as defined.

6. A compound according to claim 1, of formula (VII):

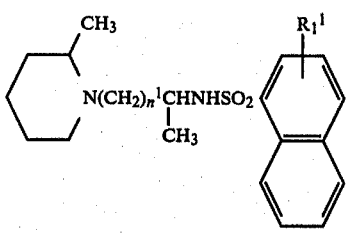

wherein:

$R_1{}^1$ is hydrogen or $C_{1-4}$ alkoxy; and $n^1$ is 1 or 2.

7. 1-[2-(4-methoxy-1-naphthalenesulphonamido)-propyl]-2-methylpiperidine, 1-[4-(1-naphthalenesulphonamdio)pentyl]-2-methyl piperidine or a pharmaceutically acceptable salt thereof.

8. A process for the preparation of a compound according to claim 1 comprising the reaction of a compound of the formula (VIII):

$$R_2N(CH_2)_nCHR_4(CH_2)_mNH_2 \qquad (VIII)$$

wherein the variables are as defined in relation to formula (I) and a compound of the formula (IX):

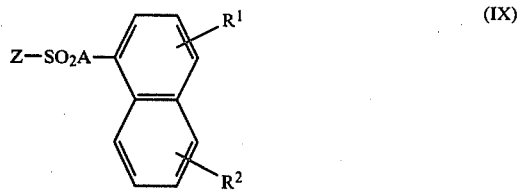

wherein Z is a group readily displaceable by a nucleophile, such as chlorine or bromine and $A, R_1{}^1$ and $R_1{}^2$ are as hereinbefore defined; and optionally forming a salt of the resultant compound of the formula (I).

9. A pharmaceutical composition for the treatment or prophylaxis of cardiac arrhythmia in mammals including humans, comprising an effective amount of a compound according to claim 1 or a pharmaceutically acceptable salt thereof, together with a pharmaceutically acceptable carrier.

10. A method of treatment or prophylaxis of cardiac arrhythmia in mammals including humans, comprising the administration to a sufferer of a therapeutically effective amount of a compound according to claim 1 or a pharmaceutically acceptable salt thereof.

11. A compound according to claim 1 wherein $R^2$ is hydrogen and $R^1$ is $C_{1-4}$ alkyl.

12. A compound according to claim 11 wherein $R_2N$ is 1-pyrrolidyl substituted by one or two methyl groups.

13. A compound according to claim 1 of formula (IV):

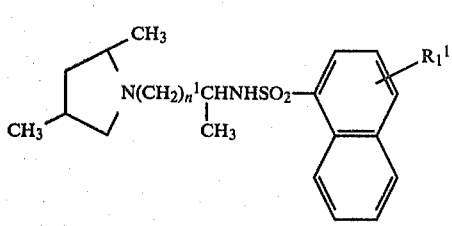

wherein $R^1{}_1$ is $C_{1-4}$ alkoxy, $C_{1-4}$ alkyl or hydrogen, and $n^1$ is 1 or 3.

14. 1-[4-(4-methoxy-1-naphthalenesulphonamido)-pentyl]-2,3-dimethylpyrrolidine or a pharmaceutically acceptable salt thereof.

* * * * *